(12) United States Patent
Radhakrishnen et al.

(10) Patent No.: US 12,266,185 B2
(45) Date of Patent: Apr. 1, 2025

(54) METHOD AND SYSTEM FOR REAL-TIME HEALTH MONITORING AND ACTIVITY DETECTION OF USERS

(71) Applicants: Arvind Radhakrishnen, Tega Cay, SC (US); Manish Purohit, Flower Mound, TX (US); Sahil Sharma, Deerfield, IL (US)

(72) Inventors: Arvind Radhakrishnen, Tega Cay, SC (US); Manish Purohit, Flower Mound, TX (US); Sahil Sharma, Deerfield, IL (US)

(*) Notice: Subject to any disclaimer, the term of this patent is extended or adjusted under 35 U.S.C. 154(b) by 182 days.

(21) Appl. No.: 17/986,998

(22) Filed: Nov. 15, 2022

(65) Prior Publication Data

US 2023/0071470 A1  Mar. 9, 2023

(51) Int. Cl.
| | | |
|---|---|---|
| *H04N 7/18* | (2006.01) | |
| *G06V 10/774* | (2022.01) | |
| *G06V 20/40* | (2022.01) | |
| *G06V 20/52* | (2022.01) | |
| *G16H 40/67* | (2018.01) | |
| *G16H 50/20* | (2018.01) | |

(52) U.S. Cl.
CPC ............ *G06V 20/52* (2022.01); *G06V 10/774* (2022.01); *G06V 20/41* (2022.01); *G06V 20/46* (2022.01); *G16H 40/67* (2018.01); *G16H 50/20* (2018.01); *H04N 7/181* (2013.01)

(58) Field of Classification Search
CPC ........ G06V 20/52; G06V 20/46; G06V 20/41; G06V 10/774; G16H 40/67; G16H 50/20; H04N 7/181
USPC ......................................................... 348/159
See application file for complete search history.

(56) References Cited

U.S. PATENT DOCUMENTS

| | | | | |
|---|---|---|---|---|
| 11,003,914 | B2* | 5/2021 | Imes | H04N 23/80 |
| 11,968,353 | B2* | 4/2024 | Stewart | H04N 17/002 |
| 2021/0063214 | A1* | 3/2021 | Li | G01D 21/02 |
| 2021/0312236 | A1* | 10/2021 | Goncharov | G06N 20/00 |
| 2024/0054788 | A1* | 2/2024 | Renduchintala | G16Y 10/60 |

* cited by examiner

*Primary Examiner* — Trang U Tran (57) ABSTRACT

The present disclosure provides a system for real-time health monitoring of one or more users. The system includes a computing device associated with a facility, a plurality of cameras, an AI edge device, and a communication network. Moreover, the system includes a server, a database, and a notification interface. The AI edge device monitors the health of one or more users in real-time. The AI edge device monitors the health of the one or more users by processing a video feed captured by the plurality of cameras. Further, the AI edge device notifies the health-related issues in real-time using the notification interface to a first set of users.

20 Claims, 5 Drawing Sheets

METHOD AND SYSTEM FOR REAL-TIME HEALTH MONITORING AND ACTIVITY DETECTION OF USERS

TECHNICAL FIELD

The present invention relates to the field of health monitoring. More particularly, the present invention relates to a method and system for real-time health monitoring and activity detection of users.

INTRODUCTION

This invention relates generally to methods and systems for monitoring a person. Over the past few years, more people are getting concerned about the health of their family and relatives. Due to the modem working environment and busy schedule, people of old age and kids are usually left unattended without any proper supervision. In addition, with the increasing population, healthcare resources are getting scarce and healthcare officials are trying to keep the resources available for the needy. To achieve that, health monitoring systems are being used widely in hospitals and home environments. Healthcare officials and people, in general, are seeking help from autonomous health monitoring systems with minimum human interaction. In addition, health monitoring systems are required to generate legit alerts and fewer or no false alerts. Further, the health monitoring systems are required to notify the healthcare services of the generation of alerts related to any activity associated with a user being monitored as soon as possible. However, the present health monitoring systems are not able to detect the activities in an inefficient manner. Further, the present health monitoring systems take more time to generate notifications. Furthermore, the present health monitoring systems generate false alerts. Thus, there exists a need for a technical and reliable solution that can overcome the existing limitations.

SUMMARY

The present invention discloses a method and system for real-time health monitoring and activity detection of one or more users in a facility. The system includes a computing device associated with the facility, a plurality of activity detection sensors (such as cameras) installed in the facility, and a communication network. The system further includes a server, a database, and a notification interface. Also, the system further includes an AI edge device and a privacy manager. The AI edge device is a computing machine that is configured to monitor the health of the one or more users in the facility in real-time. The AI edge device monitors the health of the one or more users by processing a video feed captured by the plurality of cameras in the facility. Further, the AI edge device predicts health-related issues in real-time based on the detected activities and notifies to a first set of users using the notification interface. The facility refers to a working environment of the interactive computer environment. The facility includes the plurality of cameras that may be installed in different positions to capture all possible areas of the facility. The plurality of cameras may include image-capturing devices or sensors (such as video cameras) that can be used to capture or record a video of the facility. The AI edge device receives the video feed from each of the plurality of cameras in the facility. The captured video feed is then processed by the AI edge device to generate a 3D map or vision of the facility. The 3D video map or vision may then be used to identify one or more activities of the one or more users in the facility. Based on the detected activities, the health conditions of the one or more users are monitored in real-time. The AI edge device is a computing device to process the video feed received from each of the plurality of cameras. The AI edge device processes the video feed from each of the plurality of cameras to generate the 3D map of the facility. Furthermore, the system includes a notification interface. The notification interface provides notifications to the first set of users in real time. The first set of users may be notified based on the generation of real-time alerts. Furthermore, the system includes the privacy manager that is configured to manage the privacy of the one or more users during the capturing process inside the facility or after processing the captured video feed by the AI edge device. The system may be based on techniques such as Deep Neural Networks (DNNs), Recurrent Neural Networks (RNNs), Long Short-Term Memory (LSTM), Convolutional Neural Networks (CNNs), or a combination of the techniques, but should not be construed as limiting to the scope of the present invention. Model examples may include but are not limited to, Alexnet, MobileNet, Inception, DarkNet, DeepLab, Faster R-CNN, UNet, SegNet, Mask R-CNN, Pose3CD, Mediapipe, EfficientNet Exception models, or the like. The system uses one or more techniques to get the desired result. The system uses one or more pre-trained models from YOLO, SSD, Cafe, OpenPose, or the like. The system further uses one or more algorithms (classification algorithms such as Random Forest Classifier, Extra Trees Classifier, Ada Boost Classifier, LR, SVC, KNN, Decision Tree Classifier, LightGbm, CatBoost, or the like) to perform and execute one or more processes of the disclosed method. These and other features and advantages of the present invention will become apparent from the detailed description below, considering the accompanying drawings.

BRIEF DESCRIPTION OF THE DRAWINGS

Having thus described the invention in general terms, reference will now be made to the accompanying drawings, which are not necessarily drawn to scale, and wherein:

It should be noted that the accompanying figures are intended to present illustrations of exemplary embodiments of the present disclosure. These figures are not intended to limit the scope of the present disclosure. It should also be noted that accompanying figures are not necessarily drawn to scale.

DETAILED DESCRIPTION

In the following description, for purposes of explanation, numerous specific details are set forth in order to provide a thorough understanding of the present technology. It will be apparent, however, to one skilled in the art that the present technology can be practiced without these specific details. In other instances, structures and devices are shown in block diagram form only in order to avoid obscuring the present technology.

Reference in this specification to "one embodiment" or "an embodiment" means that a particular feature, structure, or characteristic described in connection with the embodiment is included in at least one embodiment of the present technology. The appearance of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

Reference will now be made in detail to selected embodiments of the present disclosure in conjunction with accompanying figures. The embodiments described herein are not intended to limit the scope of the disclosure, and the present disclosure should not be construed as limited to the embodiments described. This disclosure may be embodied in different forms without departing from the scope and spirit of the disclosure. It should be understood that the accompanying figures are intended and provided to illustrate embodiments of the disclosure described below and are not necessarily drawn to scale. In the drawings, like numbers refer to like elements throughout, and the thicknesses and dimensions of some components may be exaggerated for providing better clarity and ease of understanding.

It should be noted that the terms "first", "second", and the like, herein do not denote any order, quantity, or importance, but rather are used to distinguish one element from another. Further, the terms "a" and "an" herein do not denote a limitation of quantity, but rather denote the presence of at least one of the referenced items.

Figure 1A:
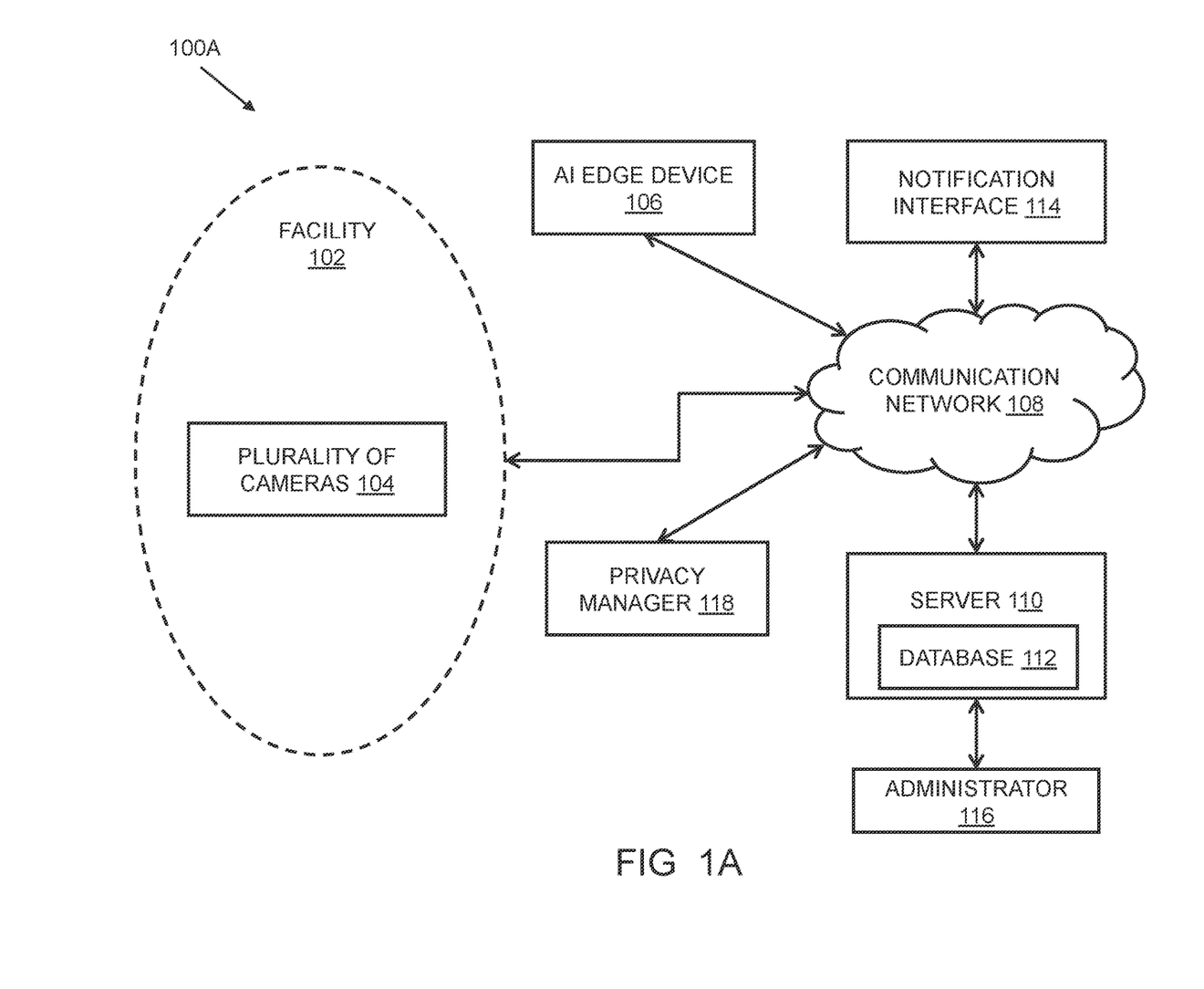
FIG. 1A illustrates an interactive system environment for real-time health monitoring and activity detection of one or more users associated with a facility, in accordance with various embodiments of the present disclosure.

FIG. 1A illustrates a system environment 100A for real-time health monitoring and activity detection of one or more users associated with a facility 102, in accordance with various embodiments of the present disclosure. The real-time health monitoring and activity detection of the one or more users are done to notify other users such as relatives and health care officials about the real-time state and condition of the one or more users from a remote location. The one or more users may include old-aged people, kids, disabled individuals, or anyone who requires constant monitoring in real-time. The system environment 100A includes a plurality of cameras 104 and an AI edge device 106. In addition, the system environment 100A includes a communication network 108, a server 110, a database 112, a notification interface 114, an administrator 116, and a privacy manager 118. Various components (as shown) interact with each other via the communication network 108.

The AI edge device 106 is a computing device, a software framework, or a combination thereof, that may facilitate the implementation of one or more applications associated with health monitoring and activity detection. Examples of the AI edge device 106 include, but are not limited to, a personal computer, a laptop, or a network of computer systems. The AI edge device 106 may be realized through various hardware such as, but not limited to, Raspberry Pi, FGPA, Movidius, Banana Pi, Nvidia Jetson T2, Arduino, Qualcomm, or the like. The AI edge device 106 may be realized through various web-based technologies such as, but not limited to, a Java web-framework, a .NET framework, a PHP (Hypertext Pre-processor) framework, or any other web-application framework. The AI edge device 106 may operate on one or more operating systems such as Windows, Android, Unix, Ubuntu, Mac OS, or the like. Various operations of the AI edge device 106 may be dedicated to the execution of procedures, such as, but are not limited to, programs, routines, or scripts stored in one or more memory units for supporting its applied applications and performing one or more operations. The AI edge device 106 may be realized by using various computer vision libraries such as, but not limited to, OpenCV, DLib, OpenALPR, OpenFace, Point Cloud, OpenPano, OpenBR, or the like. The AI edge device 106 may be realized by using various deep learning libraries such as, but not limited to, TensorFlow, Pytorch, MACE, MXNet, Spacy, CNTK, Sci-Kit Learn, Keras, Theano, or the like. The AI edge device 106 may be based on techniques such as Deep Neural Networks (DNNs), Recurrent Neural Networks (RNNs), Long Short-Term Memory (LSTM), Convolutional Neural Networks (CNNs), or a combination of the techniques. Model examples may include but are not limited to, Alexnet, MobileNet, Inception, DarkNet, DeepLab, Faster R-CNN, UNet, SegNet, Mask R-CNN, Pose3CD, Mediapipe, EfficientNet Exception models, ShuffleNet, or the like. The AI edge device 106 uses one or more techniques to get the desired result. The AI edge device 106 uses one or more pre-trained models from YOLO, SSD, Cafe, OpenPose, or the like. The AI edge device 106 further uses one or more algorithms (classification algorithms such as Random Forest Classifier, Extra Trees Classifier, Ada Boost Classifier, LR, SVC, KNN, CNN, Decision Tree Classifier, LightGbm, CatBoost, or the like) to perform and execute one or more processes of the disclosed method. Other algorithms may include but are not limited to a recursive algorithm, divide and conquer algorithm, dynamic programming algorithm, greedy algorithm, brute force algorithm, linear regression algorithm, logistic regression algorithm, KNN, CNN, or the like. Algorithms associated with object detection, facial detection, boundary box detection, multi-human detection, or the like, such as YOLO, may also be used by the AI edge device 106 to process and execute related tasks and operations associated with health monitoring and activity detection of the one or more users in the facility 102. Further, the Efficient Net B4 model may be used for activity detection in real-time.

In an embodiment, the AI edge device 106 monitors the health and activities of the one or more users in real-time. The AI edge device 106 monitors the health and activities of the one or more users by processing a video feed captured by the plurality of cameras 104. The AI edge device 106 processes the video feed received from each of the plurality of cameras 104. The AI edge device 106 processes the video feed to generate a 3D map or visual (for example, in a metaverse environment) of the facility 102. The 3D video map or visual may then be processed to identify one or more activities of the one or more users in the facility 102. Based on the detected activities, the health conditions of the one or more users are monitored in real-time. Furthermore, the AI edge device 106 notifies the health-related issues in real-time using the notification interface 114 to the first set of users such as one or more relatives, friends, or healthcare officials.

The plurality of cameras 104 and the AI edge device 106 are present in the facility 102. The facility 102 refers to any closed location where the one or more users are located. The facility 102 may include a room, a home, a hospital, or any other type of facility. The facility 102 includes the plurality of cameras 104. The plurality of cameras 104 are video cameras used to capture the facility 102 from multiple viewpoints or angles. These cameras 104 are installed in the facility 102 in a way to cover each and every space inside the facility 102. In an embodiment of the present disclosure, the plurality of cameras 104 are digital cameras that can be operated from a distant location with or without human intervention. The AI edge device 106 may also control the operations (such as ON-OFF, Zoom IN-OUT, or their movements along respective axes) of the cameras 104. The plurality of cameras 104 may be arranged or installed at multiple locations in the facility 102 to capture the facility 102 in three dimensions. Each of the plurality of cameras 104 generates the video feed with the one or more users present in the facility 102. In an embodiment of the present disclosure, the plurality of cameras 104 tracks the one or more users present in the facility 102. In another embodiment of the present disclosure, the plurality of cameras 104 tracks each of the one or more users present in the facility 102. The plurality of cameras 104 tracks the one or more users along with capturing the facility 102. In an embodiment of the present disclosure, the facility 102 may be arranged with any number of the plurality of cameras 104 depending on the need, or length, breadth, and height of the facility 102, and number of users inside the facility 102.

In an embodiment, the AI edge device 106 receives the video feed from each of the plurality of cameras 104 in the facility 102. The AI edge device 106 is a computing device to process the video feed received from each of the plurality of cameras 104. The AI edge device 106 processes the video feed to detect the one or more health risks associated with the one or more users. The AI edge device 106 processes the video feed using one or more hardware-run algorithms. The one or more hardware run algorithms include at least one of random forest algorithm, extra trees algorithm, ADA boost algorithm, LR, SVC, KNN, decision tree algorithm, LightGbm, CatBoost, recursive algorithm, divide and conquer algorithm, dynamic programming algorithm, greedy algorithm, or the like. Further, the one or more hardware run algorithms include at least one of brute force algorithm and backtracking algorithm. The AI edge device 106 processes the video feed from each of the plurality of cameras 104 to generate a 3D map of the facility 102. Further, the AI edge device 106 processes the 3D map to detect the presence or absence of the one or more users in the facility 102. When the one or more users are present in the facility 102, the AI edge device 106 processes the video feed to figure out one or more type of activities associated with the one or more users in the facility 102. In an embodiment, the AI edge device 106 is trained to identify the one or more type of activities from the video feed. In some cases, automated annotations may be used to identify a type of activity. In other cases, manual intervention may be used to validate the annotations. After successful identification of the one or more type of activities, the AI edge device 106 generates one or more relevant alerts with potential health risks associated with the one or more users in the facility. Also, the AI edge device 106 notifies the first set of users about one or more health risks of the one or more users in the facility 102 by communicating the relevant alerts to the users via the notification interface 114. The one or more health-related risks or issues include at least one of fall detection, fire detection, sleep detection, walking detection, sitting detection, noise detection, call-for-help detection, one or more environmental hazards, a plurality of activities of the user, and the like.

In an embodiment of the present disclosure, the AI edge device 106 may detect that the one or more users in the facility 102 are falling. In an example, a user may fall from the bed or fall suddenly while standing or collapse while standing. The AI edge device 106 detects fall of the one or more users by processing the video feed in real-time. The AI edge device 106 uses a sequential model for video processing to detect fall of the one or more users.

The AI edge device 106 tracks the one or more users in the facility 102. The AI edge device 106 processes the video feed to detect the plurality of activities of the one or more users. The plurality of activities includes at least one of falling, head injury, walking, standing, sitting, sleeping, snoring, loud noises, talking while sleeping, unresponsiveness and calling for help. Also, the plurality of activities includes at least one of urinating accidents, vomiting episodes, diarrhea episodes, rapid breathing, shallow breathing, tremors, shaking and pain behavior. In an embodiment of the present disclosure, the AI edge device 106 detects the plurality of activities of the one or more users like cough, drinking water, staggering and the like using the sequential model for video processing. The AI edge device 106 has been trained through learning algorithms to recognize the plurality of activities to enable real-time notifications and alerts. For example, each activity is annotated and is tied to one or more specific actions that can identify the activity. During the processing of the 3D map of the captured video feed, the AI edge device 106 lookouts for a specific action of a user captured in the same video feed. That action is compared with stored action patterns in the database 112. If a match is found, then the AI edge device 106 uses the stored annotations of the stored action patterns to identify the current activity of the user captured in the video feed.

In an exemplary embodiment of the present disclosure, the activity recognition may be carried out by performing feature extraction, followed by transformer model training. The feature extraction may be carried out using custom training with CNN Model after comparing multiple CNN models. For example, it may be trained with EfficientNetB4. The transformer model may be used for training the activity recognition model to recognize the different activities performed by the one or more users. For example, the classification of the plurality of activities is done through a transformer-based model. The transformer-based model performs human activity tasks and gives data. The data is based on videos from the plurality of cameras. The activities may include any of sitting, walking, coughing, falling, eating, and sleeping. The data is extracted through mobilenetV2. The mobilenetV2 receives the videos in the size of 224*224. The mobilenetV2 uses inverted residual blocks with bottlenecking features. In addition, the mobilenetV2 has a low parameter count and supports input size greater than 32*32 with large images and better performance. Further, the mobilenetV2 uses image size as the hyperparameter.

Furthermore, the image data is converted into X and Y vectors. The X vector is the featured vector for the images and the Y vector is the label vector. The data is divided into a ratio of 85% and 15%. The 85% is used in the mobilenetV2 and the 15% in testing the performance. The accuracy of detection of floor is up to 94%.

Further, the AI edge device 106 processes the video feed to detect one or more environmental hazards associated with the facility 102. The one or more environmental hazards include at least one of fire, a loose rug associated with the facility 102, a wet floor associated with the facility 102 and the like. Further, the one or more environmental hazards include at least one of obstacle in the facility 102, a box in the facility 102, a chair in the facility 102, steps on the floor and an uneven floor.

In an embodiment of the present disclosure, the AI edge device 106 detects fire in the facility 102. The AI edge device 106 detects fire by processing the video feed in real time. The AI edge device 106 uses a video processing algorithm to process the video feed to detect fire. The AI edge device 106 uses ShuffleNetV2 with an accuracy of 93%. In general, ShuffleNetV2 is a convolutional neural network optimized for a direct metric (speed) rather than indirect metrics like FLOPs. The requirements to use shufflenetV2 include the following—CUDA equal to or greater than 10.2, python equal to or greater than 3.6 and an OpenCV-contrib-python. In addition, the shufflenetV2 works on the occasion of smoke and realistically possible home fire with accuracy. The shufflenetV2 is trained to detect dangerous fires and not respond to fires such as stokes, matchsticks or lighting of cigarettes. In addition, the shufflenetV2 builds a 3-level system. The 3-level system varies the notification output based on the intensity of the fire and reduces the number of false alarms upon the fire.

In an embodiment of the present disclosure, the breathing is detected using two architectures—YOLO V3 for data preprocessing, CNN MobilenetV2 as a feature extractor and a transformer-based model. In general, the CNN MobilenetV2 delivers high accuracy while keeping the parameters and mathematical operations as low as possible to bring deep neural networks to mobile devices. In addition, the transformer-based model is used for training the features extracted by pre-trained MobilenetV2. The transformer-based model avoids recursion to allow parallel computation and reduces the drop in performances due to long dependencies. Further, the YOLO V3 carries out data preprocessing. The YOLOV3 extracts the person out of the frame followed by the remaining regions of the frame. Also, the problems faced during breathing are detected without the background as the regions of interest are the human body. The region without the human body is smoothened out as the region may not include any useful features for the YOLOV3. The hyperparameters used to train the YOLOV3 are dense layer units, dropouts, optimizers, learning rate and epochs.

Also, the AI edge device 106 processes the video feed to process the facility 102 to detect one or more entities of the facility 102. The one or more entities include at least one of bed, light, oxygen tank, oxygen tube, closet, chair, food tray, door, television, computer, laptop and objects on the floor.

In an embodiment of the present disclosure, the AI edge device 106 detects the floor or any surface of the facility 102. The AI edge device 106 detects the floor or any surface of the facility 102 by processing the video feed in real-time. The AI edge device 106 detects the floor or any surface of the facility 102 using the UNET video processing model. In general, UNET is a convolutional neural network architecture that expanded with few changes in the CNN architecture. UNET was invented to deal with biomedical images where the target is not only to classify whether there is an infection or not but also to identify the area of infection. In addition, UNET allows the use of global location and context at the same time. The UNET works with very few samples training and provides better performances for segmentation tasks. The dataset is loaded and split into train, valid and dataset. A data pipeline is set for the training and validation dataset. Further, parameters such as loss, metrics, optimizer and callbacks are defined. Furthermore, the hyper-parameters for UNET are learning rate, batch size, drop out, optimizer and epochs. The AI edge device 106 processes the video feed to detect the floor or any surface of the facility 102 with an accuracy of more than 94%.

The AI edge device 106 processes the video feed to generate alerts associated with the facility 102 and the one or more users. The AI edge device 106 generates alerts based on the detection of one or more of the fall hazards associated with the facility 102 and the plurality of activities of the one or more users. The AI edge device 106 processes the video feed and generates alerts in real time. The AI edge device 106 notifies the first set of users of the generation of alerts associated with the facility 102. The AI edge device 106 notifies the first set of users in real-time using the communication network 108 in real-time. The AI edge device 106 notifies the first set of users in one or more notification forms.

The AI edge device 106 prioritizes the one or more hardware run algorithms based on one or more contexts. The one or more contexts include at least one of scene, location and time associated with the one or more users. In an embodiment of the present disclosure, the AI edge device 106 prioritizes the context and allocates required processing resources to process the video feed. The AI edge device 106 allocated the required resources and reduces the overall system downtime.

In another embodiment of the present disclosure, the AI edge device 106 identifies schedule insight detection and maintenance based on the amount of time the one or more users spend in the facility 102. The AI edge device 106 monitors the amount of time with least movements of the one or more users and adds increased likelihood to the output of algorithms based on the same.

In yet another embodiment of the present disclosure, multiple algorithms run concurrently related to the facility 102. The AI edge device 106 trains algorithms to identify and prioritize the one or more users in the facility 102. The AI edge device trains algorithm based on at least one of better detectability (likelihood of a critical outcome), insight for the one or more users, better visibility of the one or more users, historical-critical insights for the one or more users, and completion of a sequence of insights of the one or more users.

In yet another embodiment of the present disclosure, the AI edge device 106 geo-coordinates the video feed for optimum measurements and produces algorithms with confidence. The said interferences such as fall, sleep, transitions, hazard detection, cough, staggering, and drinking water from fine-tined algorithms draw a time series baseline. The interferences are compared to the time series baseline. In addition, a plurality of models is running simultaneously for each user at home, or each user marked during any of the intake, onboarding, or setup process. Further, the base scene is identified in the absence of the user and the base scene is changed over time as objects move around the base scene. Furthermore, physical feedback is taken from the user for a system where reinforcement is required. In an example, reinforcement may be required when the interference is in the range of 50% to help reinforce learning for the algorithms. In an embodiment of the present disclosure, the interference frames are dropped after interference and analytics are kept to achieve privacy. In another embodiment of the present disclosure, a unique feature to block the capture of the plurality of cameras 104 if the person is in a certain area is established for privacy. In addition, the data of the AI edge device 106 and the plurality of cameras 104 is encrypted and secured.

Further, an inbuilt function of OpenCV and NMSBoxes is used to avoid multiple detections of the same object. In an embodiment of the present disclosure, a single frame is captured at user-set intervals to detect the change in the environment of the user. In addition, a function automatically captures the snapshot at the user-configured time intervals and stores the snapshot in the database with a timestamp and uses the snapshot for the next configuration.

The system environment 100A includes the communication network 108. The cameras 104, the AI edge device 106, the server 110, the notification interface 114, and the privacy manager 118 are connected to the communication network 108. The communication network 108 provides a medium to transfer the alerts associated with the facility 102 to the notification interface 114. In an embodiment of the present disclosure, the communication network 108 is an Internet connection. In another embodiment of the present disclosure, the communication network 108 is a wireless mobile network. In yet another embodiment of the present disclosure, the communication network 108 is a wired network with finite bandwidth. In yet another embodiment of the present disclosure, the communication network 108 is a combination of the wireless and the wired network for the optimum throughput of data transmission. In yet another embodiment of the present disclosure, the communication network 108 is an optical fiber high bandwidth network that enables a high data rate with negligible connection drops. The communication network 108 includes a set of channels. Each channel of the set of channels supports a finite bandwidth. Moreover, the finite bandwidth of each channel of the set of channels is based on the capacity of the communication network 108. The communication network 108 connects the facility 102 to the notification interface 114 using a plurality of methods. The plurality of methods used to provide network connectivity includes Bluetooth, USB, 2G, 3G, 4G, 5G, Wi-Fi, and the like.

Further, the system environment 100A includes the server 110 and the database 112. The facility 102 and the AI edge device 106 are associated with the server 110. In general, the server is a computer program or device that provides functionality for other programs or devices. The server 110 provides various functionalities, such as sharing data or resources among multiple clients or performing computation for a client. However, those skilled in the art would appreciate that the facility 102 is connected to a greater number of servers. Furthermore, it may be noted that the server 110 includes the database 112. However, those skilled in the art would appreciate that a greater number of servers include more numbers of database. The server 110 handles each operation and task performed by the AI edge device 106. The server 110 stores one or more instructions for performing the various operations of the AI edge device 106. The server 110 is located remotely from the AI edge device 106. The server 110 is associated with the administrator 116. In general, the administrator manages the different components in the facility 102. The administrator 116 coordinates the activities of the components involved in the facility 102. The administrator 116 is any person or individual who monitors the working of the facility 102 and the server 110 in real-time. The administrator 116 monitors the working of facility 102 and the server 110 through a communication device. The communication device includes a laptop, desktop computer, tablet, personal digital assistant, or the like. The database 112 stores different sets of information associated with various components of the facility 102. In general, the databases are used to hold general information and specialized data, such as data associated with the one or more users, data about the facility 102 and the like. The database 112 organizes the data using models such as relational models or hierarchical models.

The system environment 100A includes the notification interface 114. The notification interface 114 provides notifications to the first set of users in real time. The first set of users is notified of the generation of alerts by the AI edge device 106. The first set of users includes at least one of the one or more users, people related to the one or more users, and people having access to get notified. The first set of users is notified by one or more notification means. The one or more notification means may include at least one of email, SMS, MMS, notification via web interface, notification via smartphone, notification via computer, and the like. The notification data is saved in the form of notification history. The notification history is provided to the first set of users through the notification interface 114.

Figure 1B:
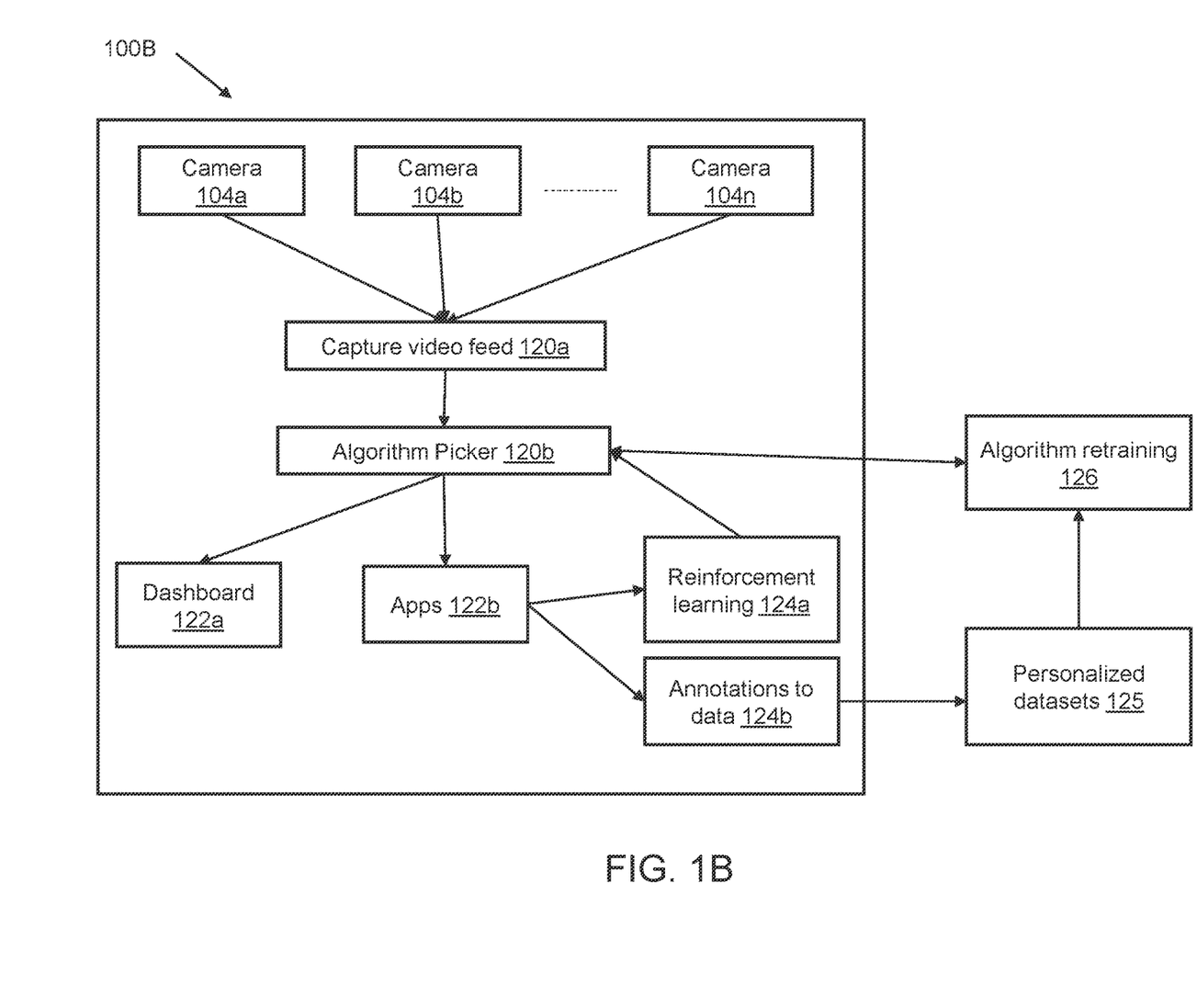
FIGS. 1B and 1C illustrate block diagrams of an interactive computing environment for real-time health monitoring and the activity detection of the one or more users, in accordance with various embodiments of the present disclosure.
Figure 1C:
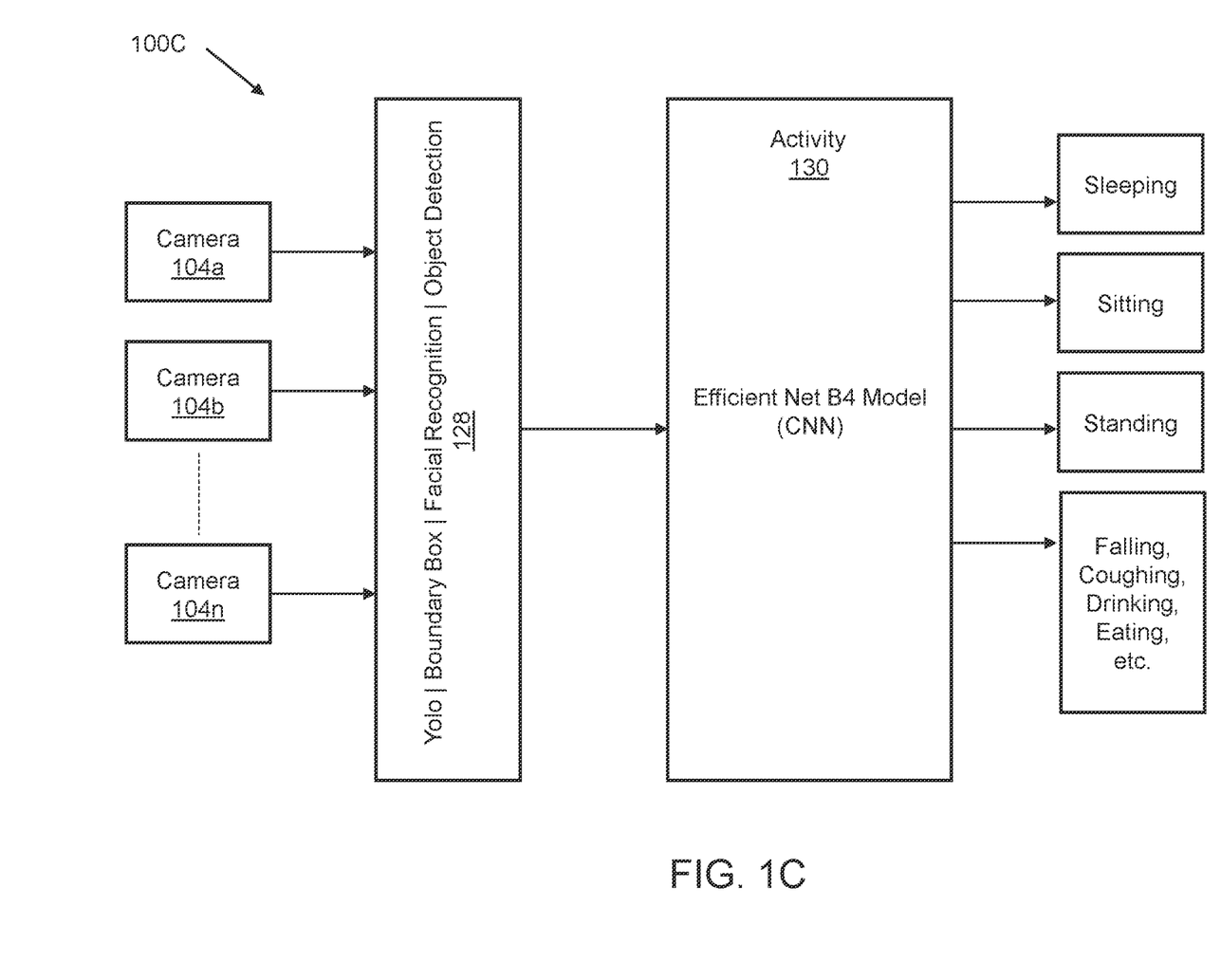

FIGS. 1B and 1C illustrate a block diagram of the interactive computing environment 100B for real-time health monitoring and the activity detection of one or more users, in accordance with various embodiments of the present disclosure. In accordance with FIG. 1B, the AI edge device 106 receives the captured video feed 120a from n number of cameras (104a, 104b, . . . , 104n) in real-time. An algorithm picker 120b chooses an algorithm from various algorithms (as mentioned above) for processing the captured video feed 120a. The AI edge device 106 then processes the captured video feed 120a to identify the one or more activities associated with the one or more users in the facility 102. Post the successful identification of the one or more activities, the AI edge device 106 generates one or more alerts and notifies the first set of users using a dashboard 122a. The algorithm picker 120b may provide the video feed 120a to an application 122b. The application 122b distributes the video feed 120a to a reinforcement learning module 124a and an annotation module 124b. The reinforcement learning module 124b may then provide feedback to the algorithm picker 120b. The annotation module 124b annotates the video feed 120a to generate personalized datasets. An algorithm retraining module receives the personalized dataset 125 to train the algorithm 126 and provides the algorithm to the algorithm picker 120b.

In accordance with FIG. 1C, the AI edge device 106 receives the video feed from each of the cameras (104a, 104b, . . . , 104n). The captured video feed is then processed by the AI edge device 106 to generate a 3D map or vision of the facility and extract features such as boundary detection, object detection, multiple human detection, action detection, facial detection, and noise or voice detection. The features may be extracted by using algorithms 128 such as YOLO algorithm, boundary box algorithm, facial recognition algorithm, object detection algorithm, or by using any suitable algorithms. Then, the AI edge device 106 uses the Efficient Net B4 Model to identify the one or more activities 130 of the one or more users based on the extracted features. Based on the detected activities, the health conditions of the one or more users are monitored in real-time. The AI edge device 106 may utilize one or more algorithms (such as random forest algorithm, extra trees algorithm, ADA boost algorithm, LR, SVC, decision tree algorithm, LightGbm, CatBoost, recursive algorithm, divide and conquer algorithm, dynamic programming algorithm, greedy algorithm, brute force algorithm, backtracking algorithm, KNN, CNN, or the like) to perform and execute one or more processes of the disclosed method. The one or more activities may be identified may include one or more of without limitation falling, head injury, walking, standing, sitting, sleeping, snoring, loud noises, talking while sleeping, unresponsiveness calling for help, urinating accidents, vomiting episodes, diarrhea episodes, rapid breathing, shallow breathing, tremors, shaking, pain behavior, cough, drinking water, staggering, or the like.

Figure 2:
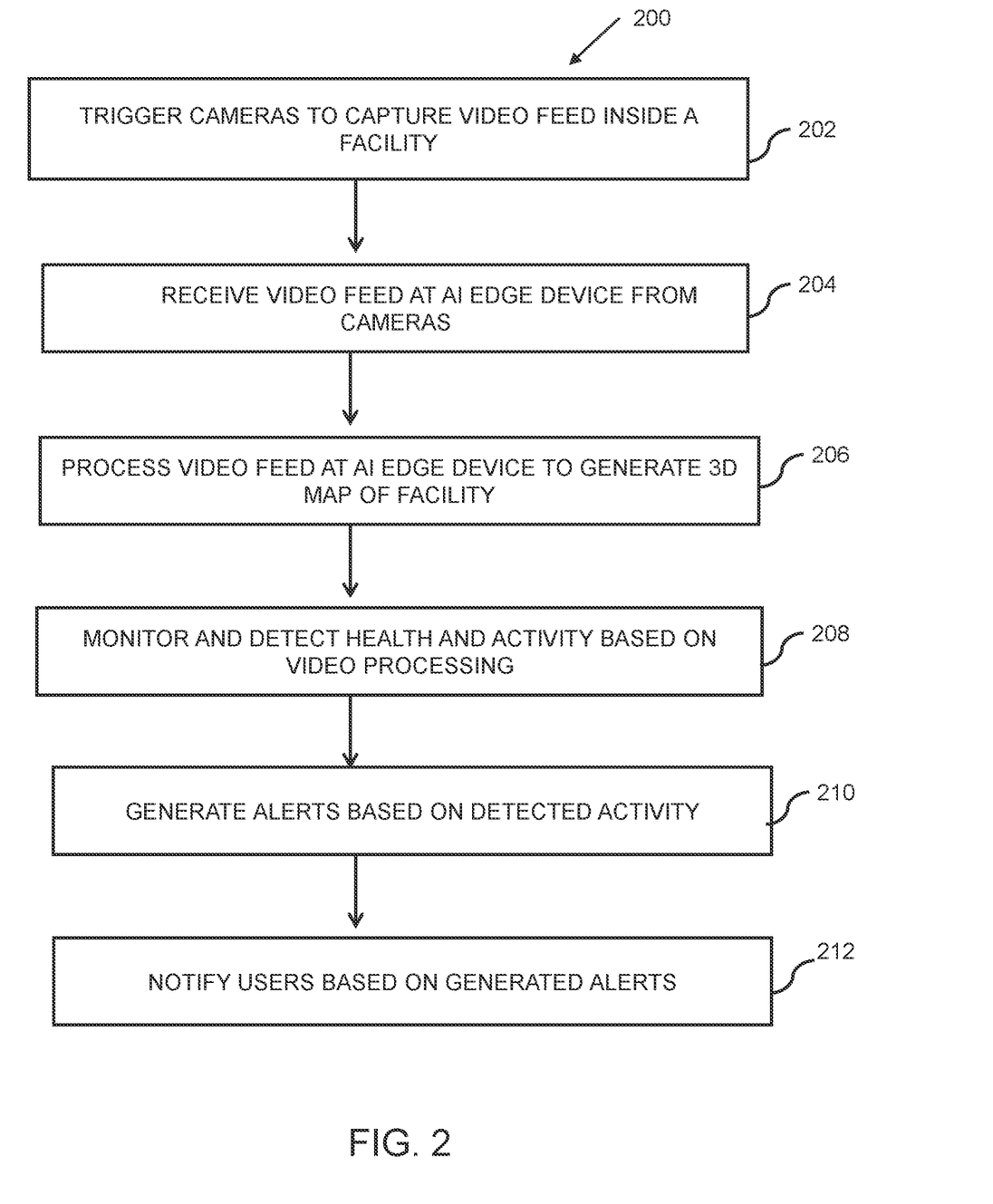
FIG. 2 illustrates a flow chart of a method for real-time health monitoring and activity detection of the one or more users, in accordance with various embodiments of the present disclosure.

FIG. 2 illustrates a flow chart 200 of a method for real-time health monitoring and activity detection of the one or more users, in accordance with various embodiments of the present disclosure. It may be noted that to explain the method steps of the flowchart 200, references will be made to the elements explained in FIG. 1A.

At step 202, the camera(s) 104 is triggered (i.e., turned ON) to capture the video feed inside the facility 102. Once the camera 104 is turned ON, the camera 104 captures and communicates the video feed to the AI edge device 106. At step 204, the AI edge device 106 receives the video feed from the camera 104. At step 206, the AI edge device 106 processes the video feed to generate the 3D map of the facility 102 and extract features from the video feed.

At step 208, the AI edge device 106 monitors and detects the health and activity of the one or more users based on the video processing. The activity recognition model pipeline may be carried out in two steps:
1. Feature Extraction Pipeline
2. Transformer Model Training Pipeline Feature Extraction Pipeline—The feature extraction may be carried out using custom training with deep learning models such as the CNN model. After comparing multiple CNN models, it was decided to train with EfficientNetB4 model. The EfficinetNetB4 model has a top-5 accuracy of 96.4% on the ImageNet dataset. The size of the model is 75 MB, and the inference time is 15.1 seconds on GPU. Although the EfficientNetB7 has the highest top-5 accuracy of 97% but the inference time is 61.6 seconds on GPU. Comparing the accuracy, inference speed and size of the model, the EfficientNetB4 has been chosen as a feature extractor. The pipeline then feed into another model to detect the pose which provide greater accuracy of slow changing activities including sleeping, standing, and sitting. Mediapipe & PoseC3d may be used for this purpose. Other model and framework examples may include Alexnet, Mobilenet, Inception, Darknet, Deeplab, Faster R-CNN, UNet, signet, Mask R-CNN, Efficientnet Exception models, or the like. The disclosed system may use one or more pre-trained models from YOLO, SSD, Cafe, or OpenPose but should not be construed as limiting to the scope of the present invention. To further improve the accuracy, the binding box is created to detect the human from other objects and take out features only for that bounding box. The bounding box then normalized to provide consistency. The object detection model runs in parallel to provide context to the activities which require objects in hand including eating and drinking to improve the accuracy. Multi-human detection is done using face detection. Frames are dropped after the inference to ensure complete privacy of the data. The bounding box is used to blur the portion of the room which requires greater privacy. The bounding box is created by extracting human features with mediapipe. The encryption is TLS 1.3 for network security. Multi-camera detection is used to allow the user to freely walk into the facility without losing much of the monitoring. The monitoring result are shown on the mobile app device for both Android and Apple devices to easily monitor the activity remotely by the caretaker. The optimizer is Stochastic Gradient Descent. Sensor data augments the CNN model for breathing.

Procedure
1. The video has been taken as an input whose frame size have been resize to (640, 640). The maximum features used is set as 500 although the model can extract 1280 features and max frames used out of the total frames present in the video is set as 25.
2. Each frame of the video is passed through the Pre-trained CNN model and the model extract the 1280 features, but we consider the $1^{st}$ 500 features and reject rest of the features.
3. The features that have been extracted is converted into NumPy format and stored in an array. This process has been carried out for all the videos.
4. The output of this pipeline is in the format of X, Y, Z, where,
   X—total number of videos in the training dataset
   Y—maximum number of frames for which the model needs to extract the features.
   Z—total number of features used out of the total number of features extracted Transformer Model Training Pipeline—The transformer model is used for training the activity recognition model to recognize the different activities performed by the users.

Procedure
1. The output of the feature extraction pipeline is split into train and test with split size set as 0.85.
2. The train split and test split has been passed through the transformer model for training the Activity Recognition Model.
3. Hyper-parameters Used
   Batch Size=32
   Epochs=200
   Optimizer=SGD (Stochastic Gradient Descent)
   Learning Rate=0.01.

Result—After training the model for 200 epochs, the accuracy came out to be 80%.

At step 210, the AI edge device 106 generates the alerts based on the detected activities. At step 212, the AI edge device 106 notifies the users on the generation of alerts.

It may be noted that the flowchart 200 is explained to have above stated process steps; however, those skilled in the art would appreciate that the flowchart 200 may have more/a smaller number of process steps which may enable all the above-stated embodiments of the present disclosure.

Figure 3:
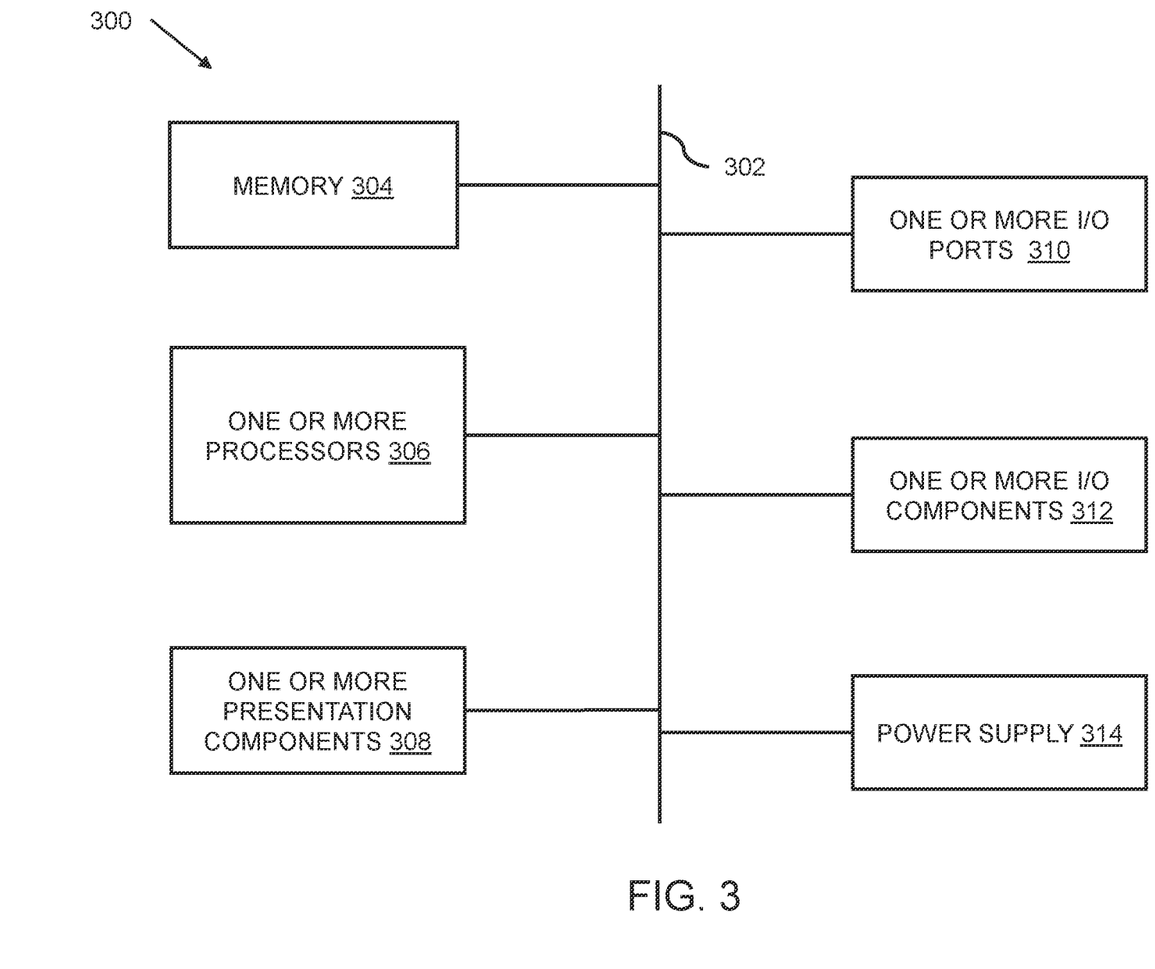
FIG. 3 illustrates a block diagram of a computing device, in accordance with various embodiments of the present disclosure.

FIG. 3 illustrates the block diagram of a computing device 300, in accordance with various embodiments of the present disclosure. The computing device 300 includes a bus 302 that directly or indirectly couples the following devices: memory 304, one or more processors 306, one or more presentation components 308, one or more input/output (I/O) ports 310, one or more input/output components 312, and an illustrative power supply 314. The bus 302 represents what may be one or more busses (such as an address bus, data bus, or combination thereof). Although the various blocks of FIG. 3 are shown with lines for the sake of clarity, in reality, delineating various components is not so clear, and metaphorically, the lines would more accurately be grey and fuzzy. For example, one may consider a presentation component such as a display device to be an I/O component. Also, processors have memory. The inventors recognize that such is the nature of the art and reiterate that the diagram of FIG. 3 is merely illustrative of an exemplary computing device 300 that can be used in connection with one or more embodiments of the present invention. Distinction is not made between such categories as "workstation," "server," "laptop," "hand-held device," etc., as all are contemplated within the scope of FIG. 3 and reference to "computing device".

The computing device 300 typically includes a variety of computer-readable media. The computer-readable media can be any available media that can be accessed by the computing device 300 and includes both volatile and nonvolatile media, removable and non-removable media. By way of example, and not limitation, the computer-readable media may comprise computer storage media and communication media. The computer storage media includes volatile and nonvolatile, removable and non-removable media implemented in any method or technology for storage of information such as computer-readable instructions, data structures, program modules or other data.

The computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information, and which can be accessed by the computing device 300. The communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Memory 304 includes computer-storage media in the form of volatile and/or nonvolatile memory. The memory 304 may be removable, non-removable, or a combination thereof. Exemplary hardware devices include solid-state memory, hard drives, optical-disc drives, etc. The computing device 300 includes one or more processors that read data from various entities such as memory 304 or I/O components 312. The one or more presentation components 308 present data indications to a subscriber or other device. Exemplary presentation components include a display device, speaker, printing component, vibrating component, etc. The one or more I/O ports 310 allow the computing device 300 to be logically coupled to other devices including the one or more I/O components 312, some of which may be built in. Illustrative components include a microphone, joystick, game pad, satellite dish, scanner, printer, wireless device, etc.

The foregoing descriptions of specific embodiments of the present technology have been presented for purposes of illustration and description. They are not intended to be exhaustive or to limit the present technology to the precise forms disclosed, and obviously many modifications and variations are possible considering the above teaching. The embodiments were chosen and described to best explain the principles of the present technology and its practical application, to thereby enable others skilled in the art to best utilize the present technology and various embodiments with various modifications as are suited to the particular use contemplated. It is understood that various omissions and substitutions of equivalents are contemplated as circumstance may suggest or render expedient, but such are intended to cover the application or implementation without departing from the spirit or scope of the claims of the present technology.

While several possible embodiments of the invention have been described above and illustrated in some cases, it should be interpreted and understood as to have been presented only by way of illustration and example, but not by limitation. Thus, the breadth and scope of a preferred embodiment should not be limited by any of the above-described exemplary embodiments.

The invention claimed is:

1. A system for health monitoring and activity detection of users, the system comprising:
a facility installed with a plurality of cameras,
wherein the cameras are configured to capture a video feed of a user in the facility, and wherein the cameras are further configured to generate a 3D map of the facility by processing the video feed; and
an AI edge device configured to:
receive the captured video feed from the cameras in real-time from the cameras, wherein the captured video feed is received in an encrypted and secured format;
process the captured video feed to detect one or more activities of the user, and generate a real-time 3D map of the facility and identify specific health-related events, based on predefined patterns, wherein the AI edge device lookouts for a specific action of the user captured in the same video feed and the action is compared with the predefined patterns, and wherein, if a match is found, then the AI edge device uses stored annotations of the predefined patterns to identify a current activity of the user captured in the video feed;
generate one or more alerts based on the detected activities; and
notify other users associated with the user based on the generated alerts via a notification interface,
wherein the above operations including the receiving, the processing, the generating, and the notifying are performed by the AI edge device on its edge and no data is transmitted over from the AI edge device to a remote server for further processing and storage.

2. The system of claim 1, wherein the cameras are digital cameras that can be operated from a distant location by the AI edge device with or without human intervention, wherein the cameras are configured to perform automatic positioning, calibration, and adjustment of focal points in response to the detected activities of the user, enabling the generation of the dynamic 3D map in real-time and wherein the cameras are installed at predefined, strategic locations in the facility to capture multi-angle, synchronized video feeds, providing full 360-degree coverage of the facility to track fine-grained user movements, such as tremors, staggering, or abnormal gait.

3. The system of claim 1, wherein the AI edge device uses one or more context-sensitive algorithms including at least Random Forest algorithm, Extra Trees algorithm, Ada Boost algorithm, LR, SVC, KNN, Decision Tree algorithm, LightGbm, CatBoost, Recursive algorithm, Divide and Conquer algorithm, Dynamic Programming algorithm, Greedy algorithm, and Brute Force algorithm, wherein the selection of algorithms is automatically adjusted based on the detected type of user activity, the environmental conditions, and the health condition of the user, to enhance the accuracy and relevance of the activity detection in real-time.

4. The system of claim 3, wherein the AI edge device further uses one or more algorithms associated with object detection, facial detection, boundary box detection, and multi-human detection while processing the captured video feed, wherein the AI edge device dynamically switches between these detection algorithms based on the position and movement patterns of the user within the facility, enabling real-time activity tracking and simultaneous detection of multiple users in different areas of the facility.

5. The system of claim 4, wherein the AI edge device further uses an Efficient Net B4 model for activity detection in real-time, and wherein the AI edge device combines Efficient Net B4 with a custom-trained neural network model for identifying subtle movements including at least tremors, micro-gestures, and slight posture changes that are indicative of health deterioration or emergency conditions, and the AI edge device prioritizes these detections for faster alert generation.

6. The system of claim 1, wherein the AI edge device is further configured to predict one or more health-related issues based on the detected activities, including detection of potential health issues including stroke or seizure based on real-time 3D skeletal mapping of the user's posture and movement patterns.

7. The system of claim 6, wherein the health-related issues include at least one of fall detection, fire detection, sleep detection, walking detection, sitting detection, noise detection, call-for-help detection, one or more environmental hazards, or a plurality of activities of the user, wherein the system detects fire hazards using smoke detection algorithms in combination with temperature sensors integrated into the cameras to correlate heat data with video input.

8. The system of claim 1, wherein the one or more activities include at least falling, head injury, walking, standing, sitting, sleeping, snoring, loud noises, talking while sleeping, unresponsiveness and calling for help.

9. The system of claim 1, wherein the one or more activities include at least urinating accidents, vomiting episodes, diarrhea episodes, rapid breathing, shallow breathing, tremors, shaking, and pain behavior.

10. The system of claim 1, wherein the one or more activities include at least coughing, drinking, and staggering.

11. The system of claim 1, further comprising a privacy manager that is configured to manage privacy of the user during or after capturing of the video feed, wherein frames are dropped after inference to ensure complete privacy of the data, and wherein the privacy manager automatically blurs identifiable features of the user when the user enters certain areas of the facility that are designated as high-privacy zones, based on user preferences stored in the system.

12. The system of claim 1, wherein the activity recognition is carried out by performing feature extraction, followed by transformer model training, wherein the transformer model is trained using an attention-based mechanism that prioritizes specific movements associated with health-related activities, such as abnormal breathing patterns or sudden limb movements.

13. The system of claim 12, wherein the feature extraction is carried out using custom training with a model selected from Alexnet, MobileNet, Inception, DarkNet, DeepLab, Faster R-CNN, UNet, SegNet, Mask R-CNN, Pose3CD, Mediapipe, EfficientNet Exception models, and ShuffleNet.

14. The system of claim 12, wherein the transformer model is used for training the activity recognition to recognize the different activities performed by the users.

15. The system of claim 12, wherein an output of the feature extraction is split into train and test with a predefined split size set, and wherein the train split and test split are passed through the transformer model for training the activity recognition.

16. The system of claim 1, wherein the AI edge device can be operated within or outside the facility with or without human intervention.

17. The system of claim 1, wherein the AI edge device identifies schedule insight detection and maintenance based on amount of time the users spend in the facility, and wherein the AI edge device monitors the amount of time with least movements of the users and adds increased likelihood to output of algorithms based on the same.

18. The system of claim 1, wherein multiple algorithms run concurrently related to the facility, wherein the AI edge device trains the algorithms to identify and prioritize the users in the facility.

19. The system of claim 18, wherein the AI edge device trains the algorithms based on at least better detectability, insight for the users, better visibility of the users, historical-critical insights for the users, and completion of a sequence of insights of the users.

20. The system of claim 1, wherein the AI edge device geo-coordinates the video feed for optimum measurements and produces algorithms with confidence.

\* \* \* \* \*